United States Patent [19]

Kalopissis et al.

[11] 4,002,634
[45] Jan. 11, 1977

[54] N-OXYPYRIDYL SUBSTITUTED CYSTEINE OR CYSTEINE DERIVATIVE THEREOF

[75] Inventors: Gregoire Kalopissis, Neuilly-sur-Seine; Claude Bouillon, Eaubonne, both of France

[73] Assignee: L'Oreal, Paris, France

[22] Filed: Sept. 15, 1975

[21] Appl. No.: 613,563

Related U.S. Application Data

[63] Continuation-in-part of Ser. No. 458,444, April 5, 1974, Pat. No. 3,917,815, which is a continuation-in-part of Ser. No. 69,936, Sept. 4, 1970, abandoned.

[30] Foreign Application Priority Data

Sept. 4, 1969 Luxembourg ............... 59405
Feb. 20, 1970 Luxembourg ............... 60384

[52] U.S. Cl. ............... 260/294.8 F; 260/294.8 G; 260/270 E
[51] Int. Cl.² ............... C07D 213/28
[58] Field of Search ... 260/294.86, 270 C, 294.8 F; 424/45, 46, 47

[56] References Cited

UNITED STATES PATENTS

| | | | |
|---|---|---|---|
| 3,033,870 | 5/1962 | Druey et al. | 260/294.8 G |
| 3,635,995 | 1/1972 | Manning | 260/294.8 G |
| 3,950,387 | 4/1976 | Joullie et al. | 260/294.8 G |

*Primary Examiner*—Alan L. Rotman
*Attorney, Agent, or Firm*—Cushman, Darby & Cushman

[57] ABSTRACT

N-oxypyridyl derivative selected from the group consisting of
a. a compound of the formula

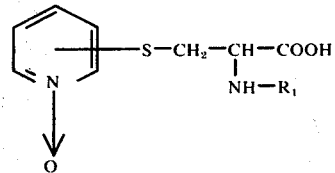

wherein the sulfur atom is attached to the N-oxypyridyl nucleus in a position ortho or para to the NO group, and $R_1$ represents hydrogen, $-COR_2$ or $-SO_2R_2$ wherein $R_2$ is alkyl having 1–4 carbon atoms, phenyl or tolyl;
b. the metal complex of the compound in (a) when $R_1$ is hydrogen; and
c. the metal salt of the compound in (a) when $R_1$ is $-COR_2$ or $-SO_2R_2$.

These derivatives are usefully employed in compositions for application to the hair, scalp or skin in order to combat the greasy and unaesthetic appearance of the hair and scalp and to counteract the formation of body odors of skin. The composition includes the said derivative of pyridine together with an appropriate carrier including, for instance, water, lower alkanol, an aqueous solution of a lower alkanol, a detergent and a cosmetic powder. The said derivative of pyridine can be included in such compositions in amounts ranging from about 0.01–10 percent by weight thereof.

4 Claims, No Drawings

N-OXYPYRIDYL SUBSTITUTED CYSTEINE OR CYSTEINE DERIVATIVE THEREOF

This application is a continuation-in-part of our application Ser. No. 458,444 filed Apr. 5, 1974, now U.S. Pat. No. 3,917,815, which in turn is a continuation-in-part of Ser. No. 69,936 filed Sept. 4, 1970, now abandoned.

The present invention relates to novel pyridine derivative compounds, to a process for preparing them and to cosmetic and deodorant compositions containing them.

The compounds of this invention have fungicidal, bactericidal and anti-dandruff characteristics and are usefully employed as an active compound in cosmetic and deodorant compositions. The active compounds of the present invention are derived from cysteine or a derivative thereof wherein the hydrogen of the thiol function of cysteine is replaced by an N-oxypyridyl radical.

The cosmetic compositions of the present invention when administered topically to a human being having hair, scalp or skin characterized by a greasy and unaesthetic appearance significantly improve the condition and appearance of the hair, scalp and skin by essentially eliminating this greasy and unaesthetic appearance. This condition of a greasy and unaesthetic appearance of the hair, scalp and skin can be occasioned by excessive secretions of the sebaceous glands and the compositions of this invention are useful in diminishing such excessive secretions.

There has already been proposed for use in combatting against the greasy appearance of the hair as well as against the unaesthetic appearance of the skin certain S-substituted derivatives of cysteine and its homologs. However, it has been found that the active compounds according to the present invention exhibit an activity greater than that of previously known compounds for combatting against a greasy and unaesthetic appearance of the hair, scalp and skin.

The deodorant compositions of the present invention when applied topically to a human being having dampness of the skin and body odors due to decomposition of the perspiration by the micro-organisms present, significantly counteract the formation of body odors by essentially inhibiting the microorganism action.

This condition of dampness of the skin and body odors can be occasioned by normal or excessive secretions of the sudoriferous glands. The deodorant compositions of this invention are very useful to combat body odors due to the anti-microbial activity of the active compounds.

Accordingly, the present invention has for an object novel compounds of the formula

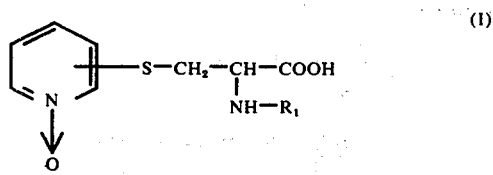

wherein
the sulfur atom is attached to the N-oxypyridyl nucleus in a position ortho or para to the NO group, and $R_1$ represents a member selected from the group consisting of hydrogen, $COR_2$ and $SO_2R_2$ wherein $R_2$ represents a member selected from the group consisting of alkyl having 1 to 4 carbon atoms, phenyl and tolyl.

When $R_1$ is hydrogen the novel compounds of this invention can also be in the form of their metal complexes, or chelates, and suitably such metals used to form the chelates are selected from the group consisting of zinc, iron (Fe II), cadmium and manganese.

These chelates have the formula:

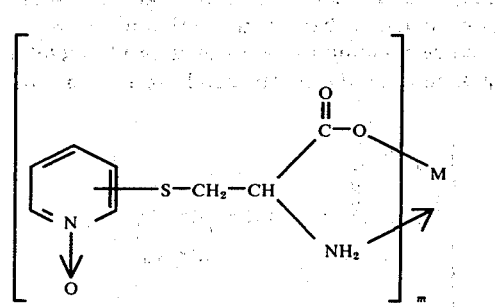

wherein:
M represents a metal selected from the group consisting of zinc, iron (Fe II), cadmium and manganese and $m$ is an integer corresponding to the valence of the metal M.

Advantageously these chelates can have the formula

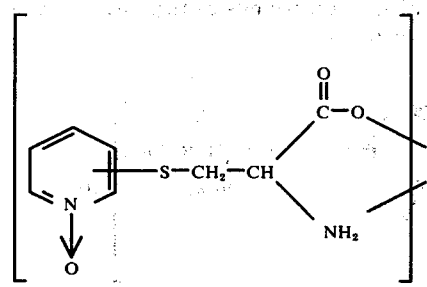

wherein $M^1$ is selected from the group consisting of zinc, iron, cadmium and manganese.

When $R_1$ is $COR_2$ or $SO_2R_2$, the novel compounds of this invention can also be in the form of their metal salts, and suitably such metals used to form these salts are selected from the group consisting of zinc, iron, manganese, tin, cadmium, titanium, aluminum, molybdenum, sodium, potassium, calcium, barium and lithium.

These salts have the formula

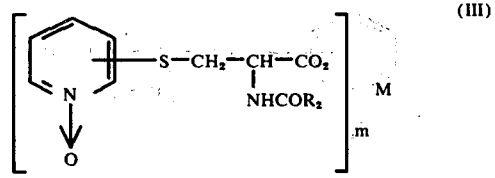

or

-continued

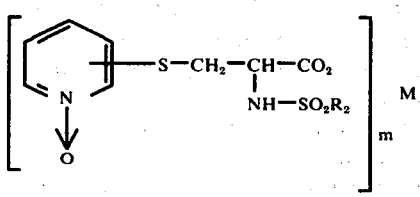

wherein $R_2$ has the meaning given above, M is selected from the group consisting of zinc, iron, manganese, tin, cadmium, titanium, aluminum, molybdenum, sodium, potassium, calcium, barium and lithium and $m$ is an integer corresponding to the valence of the metal M.

Advantageously, these salts can have the formula

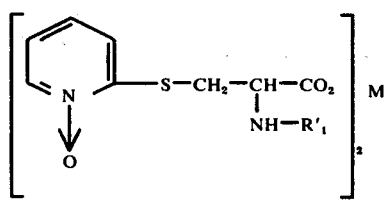

wherein $R'_1$ is selected from the group consisting of —$COR'_2$ and —$SO_2 R''_2$ wherein $R'_2$ is selected from the group consisting of alkyl having 1–4 carbon atoms and phenyl, and $R''_2$ is selected from the group consisting of alkyl having 1–4 carbon atoms, phenyl and tolyl; and M is selected from the group consisting of iron and zinc.

The present invention is also directed to the salts of the esters of the compounds of formula (I), said salts having the formula:

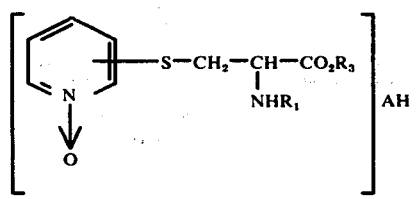

wherein
$R_1$ is selected from the group consisting of hydrogen, $COR_2$ and $SO_2R_2$ wherein $R_2$ is selected from the group consisting of alkyl having 1 to 4 carbon atoms, phenyl and tolyl, $R_3$ represents alkyl having 1 to 4 carbon atoms, and AH is an acid selected from the group consisting of hydrochloric acid, salicylic acid, malic acid, tartaric acid and maleic acid.

Advantageously, these ester salts include those of the formula

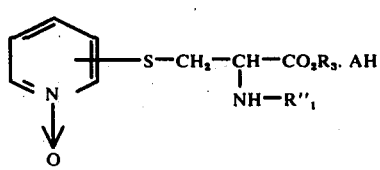

wherein $R_3$ is alkyl having 1–4 carbon atoms and $R''_1$ is selected from the group consisting of hydrogen and —$COR_2$ wherein $R_2$ is alkyl having 1–4 carbon atoms and AH is an acid selected from the group consisting of hydrochloric acid, salicylic acid, malic acid, tartaric acid and maleic acid.

Specific novel compounds of the present invention usefully employed in cosmetic compositions are:

a. S-(N-oxpypyridyl-2) L-cysteine having the formula:

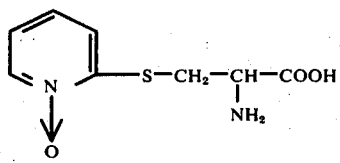

b. The dihydrochloride of the methyl ester of S-(N-oxypyridyl-2) L-cysteine having the formula:

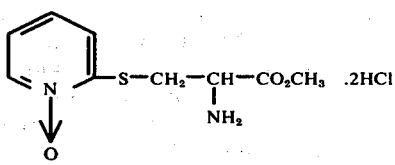

c. Salicylate of the ethyl ester of S-(N-oxypyridyl-2) L-cysteine

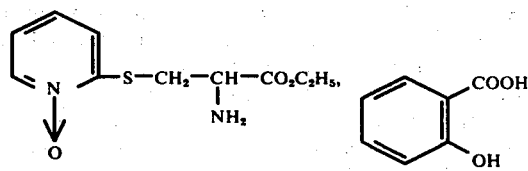

d. Tartarate of the ethyl ester of S-(N-oxypyridyl-2) L-cysteine

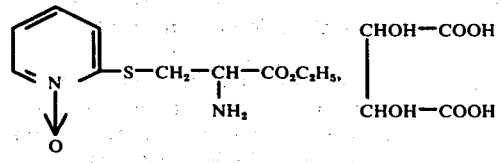

Additionally, the methyl, propyl, isopropyl and butyl esters are also employed.

e. S-(N-oxypyridyl-2)-N-acetyl L-cysteine having the formula:

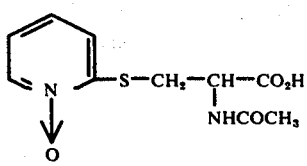

f. The zinc salt of S-(N-oxypyridyl-2)-N-acetyl-L-cysteine having the formula:

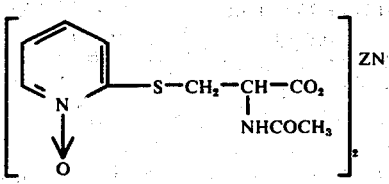
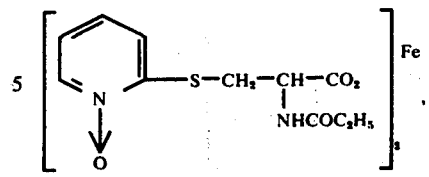

Additionally, corresponding iron, manganese, tin, cadmium, titanium, aluminum, molybdenum, sodium, potassium, calcium, barium and lithium salts are also usefully employed.

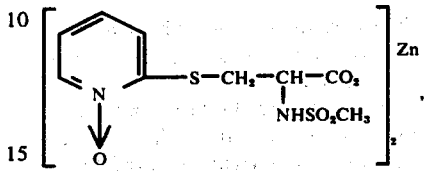

g. The zinc chelate of S-(N-oxypyridyl-2) L-cysteine having the formula:

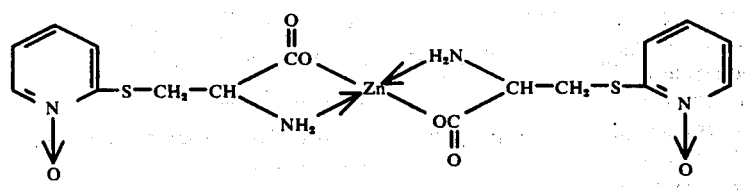

h. The iron chelate of S-(N-oxypyridyl-2) L-cysteine having the formula:

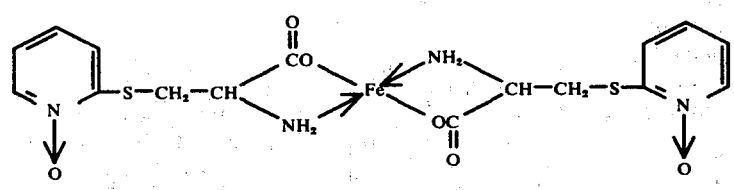

i. The cadmium chelate of S-(N-oxypyridyl-2) L-cysteine having the formula:

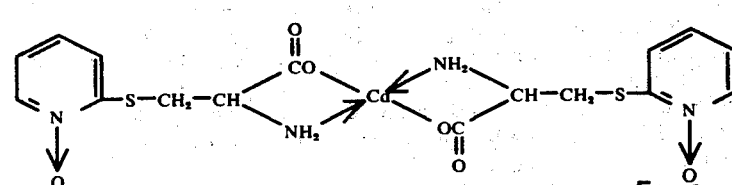

and j. The manganese chelate of S-(N-oxypyridyl-2) L-cysteine having the formula:

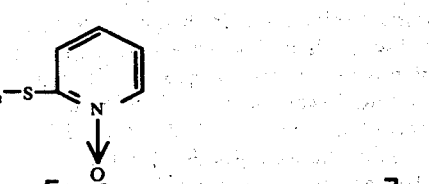, and

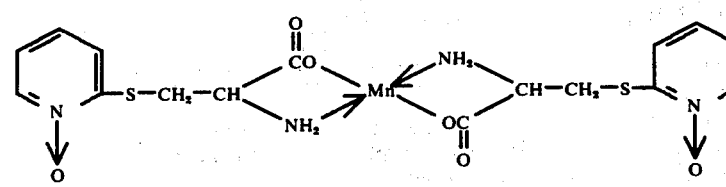

Additionally, the following compounds are also employed:

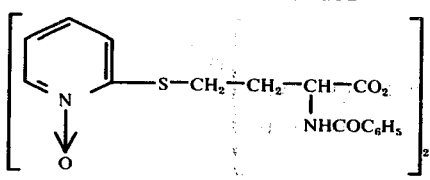

Corresponding salts of other metals such as manganese, tin, cadmium, titanium, sodium, calcium and barium are also usefully employed.

The present invention is also directed to a process of preparing the compounds of formula I. This process comprises reacting a halogen derivative (preferably, the bromide or chloride) of pyridine N-oxide with cysteine or with a derivative of cysteine, the reaction being performed in a polar solvent medium selected from the group consisting of water and dilute aqueous lower alkanol solution 20–50% by volume, said medium having a pH ranging from about 7–10 and at a temperature of at least about 10° C, preferably at least 20° C and less than about 80° C. The pH value is obtained by adding a mineral or organic base such as NaOH, KOH, NH$_4$OH, diethylamine or triethylamine, organic bases being preferred. The molar ratio of said halogen derivative of pyridine N-oxide to said cysteine or cysteine derivative is about 1–1.5:1.

The preparation of the metal salts and complexes is achieved by addition to the reaction medium containing said N-oxypyridyl derivative, an inorganic or organic salt of the metal which it is desired to make into a salt or complex. Preferably, metal acetates, metal carbonates or metal sulfates are used in essentially equimolar proportions relative to the molar concentration of the N-oxypyridyl derivative formed.

The present invention also has for an object a cosmetic composition having fungicidal, bactericidal and anti-dandruff characteristics for application to the hair, scalp or skin in order to combat the greasy and unaesthetic appearance of the hair and scalp to counteract the formation of body odors, said composition comprising a solution in a carrier selected from the group consisting of water, a lower alkanol selected from the group consisting of ethanol and isopropanol and an aqueous solution of said lower alkanol wherein said lower alkanol is present in amounts of about 20–70 percent by weight of said solution, of at least one pyridine derivative as defined above, in amounts of about 0.01–10 percent by weight of said composition.

The present invention also has for an object a pressurized sprayable aerosol cosmetic composition having fungicidal, bactericidal and anti-dandruff characteristics for application to the hair, scalp and skin in order to combat the greasy and unaesthetic appearance of the hair and scalp and to counteract the formation of body odors, said composition comprising in admixture with a member selected from the group consisting of water, ethanol, isopropanol, talcum powder and propylene glycol, at least one pyridine derivative as defined above, in amounts of about 0.01–10 percent by weight of said composition.

Yet a further object of the present invention is a cosmetic composition in the form of hair setting lacquer or lotion containing at least one pyridine derivative as defined above in an appropriate cosmetic vehicle or carrier, with at least one conventional cosmetic film forming resin, generally having a molecular weight ranging from about 10,000–700,000, the said pyridine derivative being present in amounts of about 0.5 to 6 percent by weight of said composition and said film forming resin being present in amounts of about 1–20 percent by weight of said composition.

The excellent anti-microbial activity of the active compounds have been tested against the following microorganisms: *staphylococcus epidermitis, staphylococcus aureus, sarcina lutea, Bacillus Subtillis, micrococcus aureus, aspergillus niger, Penicillium Natatum, Mucor Mucedo, saccharomyces cerevisiae, Pityrosporum ovale.*

For a better understanding of the invention, there will now be given by way of illustration examples of the preparation of the active compounds of the present invention and examples of compositions made in accordance with this invention.

PROCESS FOR THE PREPARATION OF THE COMPOUNDS OF THIS INVENTION

EXAMPLE A

Preparation of S-(N-oxypyridyl-2) L-cysteine having the formula

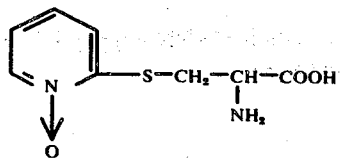

Into an aqueous solution containing 52.6 of bromo-2-pyridine-N-oxide hydrochloride, 39.6 g of L-cysteine hydrochloride and 200 cm3 of water there are slowly poured, while stirring said solution, 200 cm3 of 5N NaOH so as to maintain the pH of the solution between 8.5 and 9. The temperature of the mixture is kept at 50° C during addition of the NaOH and until the thiol groups disappear.

After cooling, the solution is contacted with a cation exchange resin (Dowex 50 in the acid or hydrogen form, having a mesh size of 100–200 mesh), which is then washed with water, and subsequently treated with a dilute ammonia solution, as an eluant, to free the product fixed on the resin. The residue obtained after evaporation of the eluate under a vacuum is crystallized in methanol.

There is obtained, with a weight yield of 81% a product in the form of white needles, which product is soluble in water and melts at 180° C with decomposition.

Elementary analysis gave the crude formula $C_8H_{10}N_2O_3S$ (M.W. = 214.2) and the following results:

|     | Calculated | Found |
| --- | --- | --- |
| C%  | 44.81 | 44.86 |
| H%  | 4.70  | 4.81  |
| N%  | 13.13 | 12.90 |

The IR spectrum of the resulting compound presents an absorption band at 1250$^{cm-1}$, which is characteristic of the N-oxide group.

Other N-oxypyridyl-2 derivatives falling within the scope of the general formula and definition given hereinbefore are also produced in an essentially similar manner. Further, such derivatives are produced using, rather than the aqueous medium defined above, an alcoholic medium (100 cm3, H₂O and 100 cm³ of a lower alkanol such as ethanol) or rather than NaOH an organic base such as diethylamine or triethylamine.

EXAMPLE B

Preparation of zinc chelate of S-(N-oxypyridyl-2) L-cysteine having the formula:

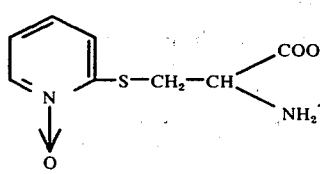

401 cm3 of 10N NaOH are poured into an aqueous solution of 217 g of bromo-2 pyridine N-oxide hydrochloride and 175.5 g of monohydrated L-cysteine hydrochloride containing 700 cm3 of water. The temperature of the mixture rises to 55° C during the addition of the NaOH and the reaction mixture is maintained at this temperature until the thiol groups disappear. The reaction mixture is then filtered, if necessary, and the pH is adjusted to 10.

Thereafter, there is added a solution of 110 g of dehydrated zinc acetate in 400 cm3 of water. A precipitate is immediately formed, which is then filtered, washed in ethanol and ether, filtered and dried under vacuum of P₂O₅.

264 g of zinc chelate of S-(N-oxypyridyl-2) L-cysteine are obtained, which is a white compound having a melting point of 245° C, with decomposition.

Analysis reveals that this chelate crystallizes with 4 to 5 molecules of water.

|  |  | NH₂ (meq/g) | Zn% |
|---|---|---|---|
| Theory | 4 H₂O | 3.54 | 11.6 |
|  | 5 H₂O | 3.44 | 12.2 |
| Found |  | 3.48 | 11.55 |

The molecular weight of the chelate, crystallized with 4 molecules of water, is 564; the molecular weight of the chelate, crystallized with 5 molecules of water, is 582.

According to the same procedure, the following chelates were prepared:

Cadmium chelate of S-(N-oxypyridyl-2) L-cysteine (from S-(N-oxypyridyl-2) L-cysteine and trihydrated cadmium acetate) white powder crystallized with two molecules of water

| Theory % Cd | 19.60 |
|---|---|
| Found % | 19.65 |

Manganese chelate of S-(N-oxypyridyl-2) L-cysteine (from S-(N-oxypyridyl)-2) L-cysteine and manganese sulfate monohydrated) quantitative yield

| Theory % Mn | 10.25 |
|---|---|

| Found % | 10.1 |
|---|---|

Iron chelate of S-(N-oxypyridyl-2) L-cysteine (from S-(N-oxypyridyl-2) L-cysteine and ferrous sulfate heptahydrated) quantitative yield in iron chelate dihydrated

| Theory % NH₂(meq/g) | 3.86 |
|---|---|
| Found % | 3.85 |

EXAMPLE C

Preparation of the dihydrochloride of the methyl ester of S-(N-oxypyridyl-2) L-cysteine having the formula:

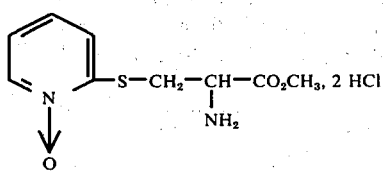

A solution of 1.5 mole of chloro-2 pyridine N-oxide and 1 mole of monohydrated L-cysteine hydrochloride in 500 cm3 of water is heated at 50° C while stirring under nitrogen atmosphere. The reaction mixture is maintained at a pH comprised between 8 and 9 by adding a diluted alkaline solution until the thiol groups disappear.

After cooling the pH is adjusted to 7 by an acidic solution and the precipitate, eventually formed, filtered. The pH is then adjusted to 5.5 and the solvent is evaporated to dryness under vacuum. The solid residue is crystallized with CHCl₃, filtered and dried.

The dried product is then treated with boiling methanol saturated with hydrochloric acid during 2 to 3 hours.

The mineral salts are filtered and by cooling there are obtained white crystals having a melting point of 200° C weight yield = 75–90%.

According to the same procedure, but replacing methanol by ethanol, propanol, isopropanol or butanol, corresponding ethyl, propyl, isopropyl and butyl esters are produced.

The melting points of these esters are as follows:

ethyl ester of S-(N-oxypyridyl-2) L-cysteine, 2 HCl F = 190° C propyl ester of S-(N-oxypyridyl-2) L-cysteine, 2 HCl F = 115° C isopropyl ester of S-(N-oxypyridyl-2) L-cysteine, 2 HCl F = 135° C butyl ester of S-(N-oxypyridyl-2) L-cysteine, 2 HCl F = 100° C

EXAMPLE D

Preparation of the salicylate of the ethyl ester of S-(N-oxypyridyl-2) L-cysteine having the formula:

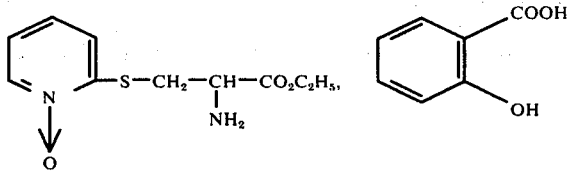

Into a solution of 15.75 g of dihydrochloride of the ethyl ester of S-(N-oxypryridyl-2) L-cysteine in 100 cm3 of ethanol previously cooled at −10° C there are poured a cooled solution of 2.3 g of sodium in 100 cm3 of ethanol. The sodium chloride is filtered and to the remaining solution 13.8 g of salicylic acid are added. After one night at −10° C, the precipitate formed is filtered. There is obtained with a weight yield of 80% a product melting at 90° C.

| Analysis: | Theory % | N | 7.36 | S | 8.43 |
|---|---|---|---|---|---|
|  | Found % |  | 7.09 |  | 8.68 |

In a similar procedure the tartarate is obtained by replacing salicylic acid by tartaric acid. After crystallization, in a mixture of ethanol/ethyl acetate, it is obtained a white product melting at 148° C.

| Analysis: | Theory % | N | 6.83 | S | 7.81 |
|---|---|---|---|---|---|
|  | Found % |  | 7.14 |  | 8.18 |

In a manner essentially the same as that set forth in Examples A, B, C and D, except for the initial cysteine reactant which is replaced with one which yields the desired product, other compounds of this invention are also produced. Thus, replacing the L-cysteine hydrochloride in Example A, for instance, with the N-acetyl derivative thereof in comparable amounts and using the same operating principles set forth in Example A produces S-(N-oxypyridyl-2)-N-acetyl L-cysteine. The metal salts and chelates of these compounds are also produced by reacting the same with stoichiometric amounts of a water soluble metal inorganic or organic salt such as the acetate, carbonate or sulfate thereof. Thus such salts as the zinc, iron, manganese, tin, cadmium, titanium, aluminum, molybdenum, sodium, potassium, calcium, barium and lithium salts are also prepared using the operating principles set forth in Examples A and B.

USE OF THE COMPOUNDS OF THIS INVENTION

EXAMPLE 1

A liquid soap is made by producing the following mixture:

| | |
|---|---|
| Sodium lauryl sulfate oxyethylenated with 2 moles of ethylene oxide | 40 g |
| Sodium N-acyl sarcosinate having the formula RCON—CH$_2$—COONa<br>                               |<br>                              CH$_3$ | |
| wherein R is lauryl | 10 g |
| Isopropyl palmitate | 5 g |
| 20% sodium chloride | 35 g |
| S-(N-oxypyridyl-2) L-cysteine | 2 g |
| Demineralized water sufficient for | 100 g |

EXAMPLE 2

A deodorant talcum powder is made according to the invention by mixing:

| | |
|---|---|
| Talcum powder | 99 g |
| Glycerin oleate | 3 g |
| Isopropyl myristate | 7 g |
| S-(N-oxypyridyl-2) L-cysteine | 3 g |
| Perfume | 2 cm$^3$ |

This talcum powder based composition is also prepared in the form of a pressurized aerosol spray by admixing under pressure 10 g of the above preparation with 45 g of a liquefied fluorochlorinated hydrocarbon, known as Freon 11 (trichloromonofluoromethane) and 45 g of a liquefied fluorochlorinated hydrocarbon known as Freon 12 (dichlorodifluoromethane).

EXAMPLE 3

A deodorant stick having the following composition is made according to the invention:

| | |
|---|---|
| Sodium stearate | 5 g |
| Propylene glycol | 60 g |
| Glycerin | 5 g |
| S-(N-oxypyridyl-2) L-cysteine | 2 g |
| Perfume | 0.5 g |
| Water sufficient for | 100 g |

EXAMPLE 4

A deodorant milk having the following composition is made according to the invention:

| | |
|---|---|
| A mixture of polyoxyethylene alcohols containing 16 to 18 carbon atoms and known as "Cire de Sipol A.O." | 2.5 g |
| Wheat starch | 2 g |
| G.4 (2-2'-dihydroxy-5-5' dichlorodiphenyl methane | 0.1 g |
| S-(N-oxypyridyl-2) L-cysteine | 2 g |
| Ethylenediaminetetraacetic acid, sodium salt | 0.1 g |
| Methyl parahydroxybenzoate | 0.1 g |
| Silicone oil known commercially as "Rhodorsil 47 V 300" | 0.2 g |
| Water sufficient for | 100 g |

EXAMPLE 5

A deodorant cream having the following composition is made according to the invention:

| | |
|---|---|
| Nonionic self-emulsifiable fatty alcohol complexes known commercially as "Lambritol Wax 21" | 21 g |
| Isopropyl myristate | 3 g |

-continued

| | |
|---|---|
| Silicone oil known as "Rhodorsil 47 V 300" | 0.5 g |
| Propylene glycol | 2 g |
| Propyl parahydroxybenzoate | 0.2 g |
| Salicylate of the ethyl ester of S-(N-oxypyridyl-2) L-cysteine | 2 g |
| Perfume | 1 g |
| Water sufficient for | 100 g |

EXAMPLE 6

A deodorant toilet water according to the invention is prepared by making the following mixture:

| | |
|---|---|
| S-(N-oxypyridyl-2) L-cysteine | 2 g |
| Perfume | 1 g |
| Absolute ethyl alcohol | 50 cm³ |
| Water sufficient for | 100 cm³ |

EXAMPLE 7

A capillary lotion according to the invention is prepared by dissolving in 100 cm³ of perfumed distilled water, 1.5 g of S-(N-oxypyridyl-2) L-cysteine.

EXAMPLE 8

A men's hair dressing lotion is prepared by mixing:

| | |
|---|---|
| Dihydrochloride of propylester of S-(N-oxypyridyl-2) L-cysteine | 0.75 g |
| Dimethylhydantoin formol resin | 0.5 g |
| Dimethyl dilaurylammonium chloride | 0.5 g |
| Perfume | 0.1 g |
| Ethyl alcohol | 50 cc |
| Water sufficient for | 100 cc |

EXAMPLE 9

A capillary composition according to the invention is prepared by mixing:

| | |
|---|---|
| S-(N-oxypyridyl-2) L-cysteine | 1.5 g |
| Perfumed distilled water | 100 cc | to which are added:

| | |
|---|---|
| Reticulated polyacrylic acid known under the trademark "Carbopol 940" | 1.25 g |

To the resulting mixture there is added sufficient ammonia to obtain a pH between 8.0 and 8.2. This mixture is in the form of a gel.

EXAMPLE 10

A capillary lotion made in accordance with this invention is prepared by dissolving 3 g of S-(N-oxypyridyl-2) L-cysteine in 100 cm³ of 50% ethanol or isopropanol solution.

EXAMPLE 11

A liquid shampoo according to the invention is prepared by mixing the following compounds:

| | |
|---|---|
| Sodium lauryl sulfate oxyethylenated with 2.2 moles of ethylene oxide | 9 g |
| Sodium monolauryl sulfosuccinate | 1 g |
| Polyethylene glycol distearate | 2 g |
| Lauric diethanolamide | 2 g |
| Cadmium chelate of S-(N-oxypyridyl-2) L-cysteine | 0.3 g |
| Perfume | 0.3 g |
| Lactic acid sufficient for pH of 6.5 | |
| Water sufficient for | 100 g |

EXAMPLE 12

A cream shampoo according to the invention is made by mixing the following compounds:

| | |
|---|---|
| Sodium lauryl sulfate | 10 g |
| Product of condensation of copra fatty acids on methyltaurine (a paste sold under the tradename "Hostapon C.T." by the Hoechst Company and having the formula: R—CON—CH$_2$—CH$_2$—SO$_3$Na, $\quad\quad\quad\;\;$ \| $\quad\quad\quad\;\;$ CH$_3$ wherein R represents the copra radical C$_5$ to C$_{17}$) | 45 g |
| Lauryl monoethanolamide | 2 g |
| Glycerol monostearate | 4 g |
| Butylester of S-(N-oxypyridyl-2) L-cysteine, 2 HCl | 2 g |
| Lactic acid sufficient for pH of 6.6 | |
| Perfume | 0.2 g |
| Water sufficient for | 100 g |

EXAMPLE 13

A shampoo powder made in accordance with the present invention is prepared by mixing:

| | |
|---|---|
| Sodium lauryl sulfate | 40 g |
| The product of condensation of copra fatty acids on sodium isethionate (sold under the tradename "Hostapon K.A." by the Hoechst company and having the formula: R COO—CH$_2$—CH$_2$SO$_3$Na, wherein R represents the copra radical C$_5$ to C$_{17}$) | 31 g |
| S-(N-oxypyridyl-2) L-cysteine | 28 g |
| Perfume | 1 g |

At the time of use, the powder is dissolved in 10 times its weight of water, the solution then being applied to the head.

EXAMPLE 14

A dye shampoo made in accordance with this invention is prepared by mixing:

| | |
|---|---|
| Iron chelate of S-(oxypyridyl-2) L-cysteine | 5 g |
| Ammonium lauryl sulfate oxyethylenated with 2 moles of ethylene oxide | 250 g |
| Paratoluylenediamine | 10 g |
| Metadiamino anisol sulfate | 0.5 g |
| Resorcinol | 5 g |
| Metaaminophenol | 1.5 g |
| Paraaminophenol | 1 g |
| Ethylene diamine tetracetic acid | 3 g |
| 40% sodium bisulfite | 15 g |

-continued

| Water sufficient for | 1000 g |

This product is mixed with 1000 g of 20 volume hydrogen peroxide and hair containing 80% white hair is impregnated with this composition. A brown coloring is obtained.

EXAMPLE 15

The first step of a permanent wave operation is performed with a composition containing:

| | |
|---|---|
| Ammonium thioglycolate | 9.5 g |
| Sipol AO wax (sold by the Sinnova company, is a mixture of 30% cetyl alcohol and 70% stearic alcohol polyoxyethylenated with 33 moles of ethylene oxide) | 0.8 g |
| Ammonia, solution sufficient for 0.7 N | |
| Water sufficient for | 100 g |

With the hair in curlers, the setting is performed with the following composition:

| | |
|---|---|
| Sodium bromate | 18 g |
| S-(N-oxypyridyl-2) L-cysteine | 0.5 g |
| Water sufficient for | 100 g |

After the hair has been rinsed, taken down and then dried, a permanent presenting a good hold is obtained, the hair becoming much less greasy than before.

EXAMPLE 16

The first step of a permanent is performed for oily hair with the two-part composition described below:
The first part contains:

| | |
|---|---|
| Ammonium thioglycolate | 9.5 g |
| Monoethanolamine sufficient for 0.65 N solution | |
| Ammonium lauryl sulfate | 0.5 g |
| Water sufficient for | 100 g |
| The second part is made up of: | |
| Isopropyl ester of S-(N-oxypyridyl-2) L-cysteine, 2 HCl | 1 g |

The second part is dissolved in the solution constituting the first part and the first step of a permanent waving is performed with this composition in a conventional manner.

EXAMPLE 17

A dermal cream is prepared by mixing the following ingredients:

| | |
|---|---|
| Tartarate of the ethyl ester of S-(N-oxypyridyl-2) L-cysteine | 2 g |
| Titanium oxide | 10 g |
| Red iron oxide | 0.3 g |
| Yellow iron oxide | 0.2 g |
| Brown iron oxide | 0.4 g |
| Chestnut iron oxide | 0.2 g |
| Oxyethylene cetyl stearyl alochol | 7 g |
| Silicone oil | 1 g |
| Polyglycol stearate | 6 g |
| Propyl parahydroxybenzoate | 0.20 g |

-continued

| Water sufficient for | 100 g |

EXAMPLE 18

An anionic liquid shampoo according to the invention is prepared by mixing the following compounds:

| | |
|---|---|
| Technical (100%) oxyethylenated sodium lauryl sulfate | 7 g |
| Copra diethanolamide | 2 g |
| "Carbopol 934" (reticulated polyacrylic acid sold by the Goodrich Company) | 0.9 g |
| Hydroxymethyl cellulose | 0.4 g |
| Cadmium chelate of S-(N-oxypyridyl-2) L-cysteine | 2 g |
| Perfume | 0.5 g |
| Dye (F.D.C. Green No. 3 having the empirical formula $C_{37}H_{34}N_2O_{10}S_3Na_2$) | 0.1 g |
| Water sufficient for | 100 g |

This shampoo is a liquid opaque suspension having a pH of 7–7.5. The shampoo is applied twice, with intermediate rinsing, in an amount sufficient to obtain the formation of a foam upon the second application.

EXAMPLE 19

An anionic liquid shampoo according to this invention is prepared by mixing the following compounds:

| | |
|---|---|
| Technical (100%) triethanolamine lauryl sulfate | 9 g |
| Copra diethanolamide | 4 g |
| "Veegum F" (highly refined colloidal magnesium-silicate- sold by the Vanderbilt company) | 5 g |
| Sodium chloride | 3 g |
| Manganese chelate of S-(N-oxypyridyl-2) L-cysteine | 2 g |
| Carboxymethyl cellulose | 0.3 g |
| Perfume | 0.5 g |
| Dye (F.D.C. Green No. 3 having the empirical formula $C_{37}H_{34}N_2O_{10}S_3Na_2$) | 0.1 g |
| Water sufficient for | 100 g |

This shampoo is in the form of an opaque liquid suspension having a pH 7–7.5.

When applied under the conditions of Example 18, it also gives good results in the case of scalp exhibiting dandruff.

EXAMPLE 20

An anionic cream shampoo is made by mixing the following compounds:

| | |
|---|---|
| Technical (100%) sodium lauryl sulfate | 10 g |
| Copra monoethanolamide | 5 g |
| Glycerol monostearate | 6 g |
| Lanolin | 1 g |
| Zinc chelate of S-(N-oxypyridyl-2) L-cysteine | 2 g |
| Dye (F.D.C. Green No. 3 having the empirical formula $C_{37}H_{34}N_2O_{10}S_3N_2$) | 0.1 g |
| Perfume | 0.5 g |
| Water sufficient for | 100 g |

This shampoo, applied under the conditions of Example 18, also gives good results in the case of scalp exhibiting dandruff.

EXAMPLE 21

A liquid soap is made by making the following mixture:

| | |
|---|---|
| Sodium lauryl sulfate oxyethylenated with two molecules of ethylene oxide | 40 g |
| Sodium N-acyl-sarcosinate having the formula: R CO—N—CH$_2$—COONa $\quad\quad\quad\quad$ \| $\quad\quad\quad\quad$ CH$_3$ wherein R is lauryl | 10 g |
| Isopropyl palmitate | 5 g |
| 20% lactic acid | 4 g |
| Cadmium chelate of S-(N-oxypyridyl-2) L-cysteine | 0.1 g |
| Demineralized water sufficient for | 100 g |

This soap is limpid and clear and has a pH of 6.5.

EXAMPLE 22

A dry spray according to the invention is made by mixing:

| | |
|---|---|
| Cetyl trimethylammonium bromide | 0.1 g |
| Polyoxyethylene fatty esters of sorbitol or polyoxyethylene sorbitan monooleate (Tween 80) | 0.4 g |
| Ethyl alcohol | 5 g |
| Perfume | 0.1 g |
| Zinc chelate of S-(N-oxypyridyl-2) L-cysteine | 0.1 g |
| Dichlorodifluoromethane (Freon 12) sufficient for | 100 g |

Before use of this dry spray, it is necessary to agitate the composition, the zinc chelate being barely soluble.

EXAMPLE 23

A dry spray according to the invention is made by mixing:

| | |
|---|---|
| Propylene glycol | 1 g |
| Iron chelate of S-(N-oxypyridyl-2) L-cysteine | 0.1 g |
| Perfume | 0.2 g |
| Dichlorodifluoromethane (Freon 12) | 100 g |

As in the preceding example, the composition is agitated before use.

EXAMPLE 24

A deodorant talcum powder in spray form is prepared by mixing:

| | |
|---|---|
| Talcum powder | 85 g |
| Glycerol oleic esters | 3 g |
| Isopropyl myristate | 7 g |
| Zinc chelate of S-(N-oxypyridyl-2) L-cysteine | 3 g |
| Perfume | 2 g |
| Propellant: | |
| Freon 11 (trichloromonofluoromethane) | 45 g |
| Freon 12 (dichlorodifluoromethane) | 45 g |

EXAMPLE 25

A solution for sanitary napkins is prepared by mixing:

| | |
|---|---|
| Sodium 1-($\beta$-carboxymethyloxyethyl)-1-(carboxymethyl)-2-(lauryl)-2-(imidazolinium) hydroxide (sold by the Miranol Chemical Co. under the trademark MIRANOL C2M | 1 g |
| Cadmium chelate of S-(N-oxypyridyl-2) L-cysteine | 0.1 g |
| 20% lactic acid | 12 cc |
| Demineralized water sufficient for | 100 g |

The solution is limpid and has a pH of 3.

EXAMPLE 26

A deodorant cream according to the invention is prepared by mixing the following material:

| | |
|---|---|
| Self-emulsifying nonionic fatty alcohol complexes (sold under the tradename "Lambritol Wax N 21") | 12 g |
| Isopropyl myristate | 3 g |
| Silicone oil (sold under the name "Rhodorsil 47 V 300") | 0.5 g |
| Propylene glycol | 2 g |
| Propyl parahydroxybenzoate | 0.2 g |
| Iron chelate of S-(N-oxypyridyl-2) L-cysteine | 1 g |
| Perfume | 1 g |
| Water sufficient for | 100 g |

EXAMPLE 27

An emulsified dilute alcohol (ethanol or isopropanol) deodorant spray according to the invention is made by making the following mixture and packaging the same under pressure in an aerosol container:

| | |
|---|---|
| Sorbitan trioleate | 0.4 g |
| Polyoxyethylene sorbitan monooleate (Tween 80) | 0.1 g |
| Manganese chelate of S-(N-oxypyridyl-2) L-cysteine | 2 g |
| Perfume | 0.8 g |
| Absolute ethyl alcohol | 22 g |
| Water | 34.7 g |
| Dichlorodifluoromethane | 40 g |

EXAMPLE 28

A deodorant toilet water according to the invention is prepared by making the following mixture:

| | |
|---|---|
| Zinc chelate of S-(N-oxypyridyl-2) L-cysteine | 0.5 g |
| Perfume | 1 g |
| Absolute ethyl alcohol | 50 cm$^3$ |
| Water sufficient for | 100 cm$^3$ |

EXAMPLE 29

A men's hair dressing lotion is prepared by mixing:

| | |
|---|---|
| Zinc chelate of S-(N-oxy-pyridyl-2) L-cysteine | 0.75 g |
| Dimethylhydantoin formaldehyde resin (water-soluble, softens at 59–80° C) | 0.5 g |
| Dimethyl dilaurylammonium chloride | 0.5 g |
| Perfume | 0.1 g |
| Ethanol | 50 cc |
| Water sufficient for | 100 cc |

This lotion is agitated before use.

EXAMPLE 30

A fluid hair dressing gel is prepared by mixing:

| | |
|---|---|
| Zinc chelate of S-(N-oxy-pyridyl-2) L-cysteine | 0.5 g |
| Reticulated polyacrylic acid (sold under the trademark "Carbopol 940") | 0.45 g |
| Polyvinylpyrrolidone (M.W. = 40,000) | 2 g |
| Oxyethylenated lanolin | 1 g |
| Polyethylene glycol 300 | 5 g |
| Methyl parahydroxybenzoate based preservative (sold under the trademark "Nipagine") | 0.1 g |
| Propyl parahydroxybenzoate based preservative (sold under the trademark "Nipasol") | 0.1 g |
| Perfume | 0.1 g |
| Triethanolamine sufficient for pH 8 | |
| Water sufficient for | 100 cc |

EXAMPLE 31

A hair setting dye lotion for application to white hair presenting a greasy appearance is prepared by mixing together:

| | |
|---|---|
| Polyvinylpyrrolidone (M.W. = 40,000) | 0.4 g |
| Vinyl acetate/crotonic acid copolymer, 90%/10% (having a molecular weight of 20,000 and sold by National Starch under the tradename RESYN 28.1310) | 0.2 g |
| Isopropyl alcohol sufficient for 50° titer | |
| Manganese chelate of S-(N-oxy-pyridyl-2) L-cysteine | 0.7 g |
| Aminopropylamino-1 anthraquinone | 0.03 g |
| Picramic acid | 0.017 g |
| N-γ-amino propylamino-4-N'-methyl-amino-1-anthraquinone | 0.04 g |
| Water sufficient for | 100 g |

The pH of the mixture is adjusted to a value of 7 by the addition thereto of triethanolamine.

A good hair setting lotion is obtained, which, when applied to white hair, makes it possible to give it a smoky gray glint, while essentially eliminating the initial greasy appearance thereof.

EXAMPLE 32

The first step of a conventional permanent wave technique is performed with a reducing composition containing:

| | |
|---|---|
| Ammonium thioglycolate | 9.5 g |
| Sipol AO wax (sold by the Sinnova company) | 0.8 g |
| Ammonia, solution sufficient for 0.7 N | |
| Water sufficient for | 100 g |

Thereafter, the second step of the permanent wave technique is conducted using a neutralizing composition, packaged in two parts which comprises as the first part or package:

| | |
|---|---|
| Hydrogen peroxide sufficient for | 6.6 vol. |
| Citric acid | 0.1 g |
| Water sufficient for | 100 cc | and as the second part or package a powder made up of:

| | |
|---|---|
| Zinc chelate S-(N-oxypyridyl-2) L-cysteine | 5 g |

The powder making up the second part or package is put in suspension in the hydrogen peroxide solution and the hair previously treated with the reducing composition described above and put up on curlers, is set with the said neutralizing solution.

After the hair has been rinsed and taken down and then dried, a permanent wave presenting a good hold is obtained, the hair becoming much less greasy than before.

EXAMPLE 33

A dermal foaming gel is prepared by mixing the following ingredients:

| | |
|---|---|
| Reticulated polyacrylic acid (sold under the trademark "Carbopol 934") | 25 g |
| Magnesium ethoxylauryl sulfate | 8 g |
| Glycerin | 10 g |
| Ammonia | 0.2 g |
| Zinc chelate of S-(N-oxypyridyl-2) L-cysteine | 2 g |
| Water sufficient for | 100 g |

EXAMPLE 34

A dermatological cake is prepared by mixing the following ingredients:

| | |
|---|---|
| Esters of sodium isethionate and copra fatty acids (sold under the trademark "IGEPON A" having the formula R—COO—CH$_2$—CH$_2$—SO$_3$—Na, wherein R = fatty acid derivative having from 12 to 18 carbon atoms) | 75 g |
| Lanolin derivatives (sold by CRODA under the trademark "SUPER HARTOLAN" and lecithin | 23 g |
| Zinc chelate of S-(N-oxypyridyl-2) L-cysteine | 2 g |

EXAMPLE 35

A shampoo powder according to the invention is made by mixing the following ingredients:

| | |
|---|---|
| Sodium lauryl sulfate powder with 90% active material | 35 g |
| Lithium lauryl sulfate powder | |

|  |  |
|---|---|
| with 90% material | 35 g |
| Sodium sulfate | 10 g |
| The dihydrochloride of the methyl ester of S-(N-oxypyridyl-2) L-cysteine | 20 g |

At the time of use, the above mixture is dissolved in about 10 times its weight of water and the resulting solution is then applied to the head.

EXAMPLE 36

A shampoo powder according to the invention is made by mixing the following ingredients:

|  |  |
|---|---|
| Sodium lauryl sulfate powder with 90% active material | 32 g |
| Condensation product of copra fatty acids with sodium isethionate (sold under the name of "HOSTAPON K.A." by the Hoechst company) | 45 g |
| Sodium sulfate | 5 g |
| Manganese chelate of S-(N-oxy-pyridyl-2) L-cysteine | 18 g |

At the time of use, the above mixture is dissolved in 5 times its weight of water and applied to the hair.

EXAMPLE 37

A shampoo powder according to the invention is made by mixing the following ingredients:

|  |  |
|---|---|
| Sodium lauryl sulfate powder with 90% active material | 35 g |
| Lithium lauryl sulfate powder with 90% active material | 35 g |
| Sodium sulfate | 10 g |
| S-(N-oxypyridyl-2)-N-acetyl L-cysteine | 20 g |

At the time of use, the above mixture is dissolved in about 10 times its weight of water. The resulting solution is then applied to the head.

EXAMPLE 38

A shampoo powder according to the invention is made by mixing the following ingredients:

|  |  |
|---|---|
| Sodium lauryl sulfate powder with 90% active material | 30 g |
| Condensation product of copra fatty acids with sodium isethionate (sold under the name of "HOSTAPON K.A." by the Hoechst company) | 41 g |
| Sodium sulfate | 10 g |
| Cadmium chelate of S-(N-oxy-pyridyl-2) L-cysteine | 19 g |

At the time of use, the above mixture is dissolved in 5 to 10 times its weight of water and applied to the hair.

EXAMPLE 39

A shampoo powder is made according to the invention by mixing the following ingredients:

|  |  |
|---|---|
| Sodium lauryl sulfate powder with 90% active material | 40 g |
| Lithium lauryl sulfate powder with 90% active material | 40 g |
| Sodium sulfate | 15 g |
| Iron chelate of S-(N-oxy-pyridyl-2) L-cysteine | 5 g |

At the moment of use, the above mixture is dissolved in about 10 times its weight of water, the solution then being applied to the head.

What is claimed is:

1. N-oxypyridyl derivative having the formula

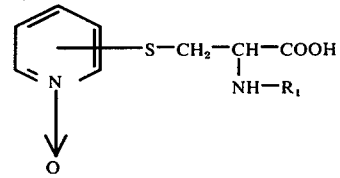

wherein the sulfur atom is attached to the N-oxypyridyl nucleus in a position ortho or para to the NO group, and $R_1$ represents a member selected from the group consisting of hydrogen, $COR_2$ and $SO_2R_2$ wherein $R_2$ is selected from the group consisting of alkyl having 1–4 carbon atoms, phenyl and tolyl.

2. A salt of N-oxypyridyl derivative having the formula

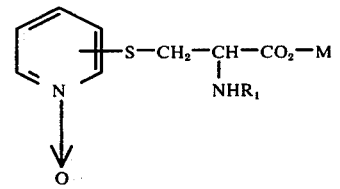

wherein the sulfur atom is attached to the N-oxypyridyl nucleus in a position ortho or para to the NO group, $R_1$ is selected from the group consisting of $COR_2$ and $SO_2R_2$ wherein $R_2$ is selected from the group consisting of alkyl having 1–4 carbon atoms, phenyl and tolyl and M is selected from the group consisting of sodium, potassium and lithium.

3. An N-oxypyridyl derivative selected from the group consisting of S-(N-oxypyridyl-2) L-cysteine, dihydrochloride of the methyl, ethyl, propyl, isopropyl and butyl ester of S-(N-oxypyridyl-2) L-cysteine, salicylate and tartarate of the ethyl ester of S-(N-oxypyridyl-2) L-cysteine and S-(N-oxypyridyl-2)-N-acetyl-L-cysteine.

4. An ester salt of N-oxypyridyl derivative having the formula

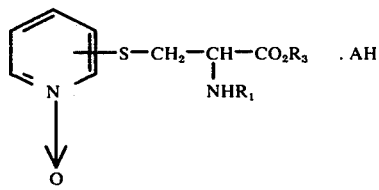

wherein $R_1$ is selected from the group consisting of hydrogen, $COR_2$ and $SO_2R_2$ wherein $R_2$ is selected from the group consisting of alkyl having 1–4 carbon atoms, phenyl and tolyl, $R_3$ is alkyl having 1–4 carbon atoms and AH is an acid selected from the group consisting of hydrochloric acid, salicylic acid, malic acid, tartaric acid and maleic acid.

* * * * *